(12) United States Patent
Swift et al.

(10) Patent No.: US 7,545,495 B2
(45) Date of Patent: Jun. 9, 2009

(54) METHODS FOR VISUALIZING CRYSTALS AND DISTINGUISHING CRYSTALS FROM OTHER MATTER WITHIN A BIOLOGICAL SAMPLE

(75) Inventors: Kerry M. Swift, Libertyville, IL (US); Edmund D. Matayoshi, Richmond, IL (US)

(73) Assignee: Abbott Laboratories, Abbott Park, IL (US)

( * ) Notice: Subject to any disclaimer, the term of this patent is extended or adjusted under 35 U.S.C. 154(b) by 13 days.

(21) Appl. No.: 11/321,993

(22) Filed: Dec. 29, 2005

(65) Prior Publication Data

US 2006/0215156 A1 Sep. 28, 2006

Related U.S. Application Data

(63) Continuation-in-part of application No. 10/832,748, filed on Apr. 27, 2004, now abandoned.

(51) Int. Cl.
*G01J 3/30* (2006.01)
*G01J 3/44* (2006.01)

(52) U.S. Cl. ........................ 356/317; 356/301

(58) Field of Classification Search ......... 356/317–318, 356/326, 301, 417; 250/458.1–461.2
See application file for complete search history.

(56) References Cited

U.S. PATENT DOCUMENTS

| | | | | |
|---|---|---|---|---|
| 5,214,288 | A * | 5/1993 | Oka et al. | 250/373 |
| 6,837,926 | B2 * | 1/2005 | David | 117/68 |
| 7,064,827 | B2 * | 6/2006 | Nurmikko et al. | 356/338 |
| 7,330,243 | B2 | 2/2008 | Betzel et al. | |
| 2002/0008871 | A1 * | 1/2002 | Poustka et al. | 356/317 |
| 2004/0007672 | A1 * | 1/2004 | DeLucas et al. | 250/373 |
| 2008/0106733 | A1 * | 5/2008 | Swift et al. | 356/317 |

FOREIGN PATENT DOCUMENTS

WO 99/05096 4/1999

OTHER PUBLICATIONS

Anderson, A.C., "The Process of Structure-Based Drug Design", *Chem. & Biol.*, 10:787-797 (2003).
Asanov, A.N., et al., "Intrinsic fluorescence as a potential rapid scoring tool for protein cytstals", *Journ of Crystal Growth*, 232:603-609 (2001).
Asher, S.A., "UV Resonance Raman Spectroscopy for Analytical, Physical, and Biophysical Chemistry",*Analy. Chem.*, 65(4):201A210A (1993).
Bourgeois, D., et al., "A microspectrophotometer for UV-visible absorption and fluorescence studies of protein crystals", *J. Appl. Cryst.*, 35:319-326 (2002).
Dong, J., et al., "Probing Inhibitors Binding to Human Urokinase Crystals by Raman Microscopy: Implications for Compound Screening", *Biochemistry*, 40(33):9751-9757 (2001).
Inoué, S., et al., "Fluorescence polarization of green fluorescence protein", *PNAS*, 99(7)):4272-4277 (2002).

(Continued)

*Primary Examiner*—Kara E Geisel
(74) *Attorney, Agent, or Firm*—Patricia Coleman-James

(57) ABSTRACT

The present invention relates to optical methods of observing, distinguishing and/or visualizing grown or nascent crystals of biological material within a biological sample.

14 Claims, 19 Drawing Sheets

OTHER PUBLICATIONS

Jancarik, J. & Kim, S-H., "Fast Communications", *J. Appl. Cryst.*, 24:409-411 (1991).

Lakowicz, J.R., "Prinicples of Fluorescence Spectroscopy", *Plenum Press*, 341-487 (1983).

Lakowicz, J.R., Principles of Fluorescence Spectroscopy, 2nd Ed., *Kluwer Academic/Plenum Publishers*, 1-23 (1999).

Lewis, E. N., et al., "Near-infrared Chemical Imaging and the PAT Initiative", *Spectroscopy*, 19(4):26-36 (2004).

Löwe, J. & Amos, L.A., "Crystal Structure of the bacterial cell-divisiion protein FtsZ", *Nature*, 391:203-206 (1998).

McCrone, W.C., et al., "Polarized Light Microscopy", *McCrone Research Institute*, v-vii (1985).

McPherson, A., "Preparation and Analysis of Protein Crystals", *Krieger Publishing Co., Inc.*, 160-180 (1982).

McPherson, A., et al., "The science of macromolecular crystallization", *Structure*, 3:759-768 (1995).

Permyakov, Eugene, et al., "Luminescent Spectroscopy of Proteins", *CRC Press, Inc.*, 35-54 (1993).

Pohl, E., et al., "Protein Crystal Identification and Localization in X-ray Crystallography", *Biophysical Journ.*, 86:397 (2004).

Puius, Y.A., et al., "Identification of a second aryl phosphate-binding site in protein-tyrosine phosphatase IB: A paradigm for inhibitor design", *PNAS*, 94:13420-13425 (1997).

Sumida, J.P., et al., "Preparation and preliminary characterization of crystallizing fluorescent derivatives of chicken egg white lysozyme", *Journ. Of Crystal Growth*, 232:308-316 (2001).

Szczepankiewicz, B.G., et al., "Discovery of a Potent, Selective Protein Tyrosine Phosphatase IB Inhibitor Using a Linked-Fragment Strategy", *J. Am. Chem. Soc.*, 125:4087-4096 (2003).

Vemede, Xavier, et al., "UV Laser-excited Flourscene as a Tool for the Visualization of Protein Crystals Mounted in Loops", *Acta Cryst.*, 253-261(2006).

Hampton Research, "Izit Crystal Dye™", www.hamptonresearch.com/hrproducts/4710.html.

* cited by examiner

UVF 6s exposure, 120 gain

Visible 1.6M ammonium sulfate
0.1M Tris pH 8.0, 23°C
18gm/ml glucose isomerase

UVF 6s exposure, 100 gain

Visible 1.6M ammonium sulfate
0.1M Bicine pH 9.0, 23°C
18mg/ml glucose isomerase

UVF 6s exposure 125 gain

Visible

15% ethanol, 0.1M HEPES pH 7.5
0.2M Magnesium chloride, 23°C
18 mg/ml glucose isomerase

UVF 6s exposure 100 gain

Visible

20% PEG1000, 0.2M MgCl2
0.1M Na cacodylate pH 6.5, 23°C
18 mg/ml glucose isomerase Visible | UV fluorescence

*Salt crystals*

Confirmed by X-ray diffraction experiments.

UVF | Visible (stereomicroscope)

Slight movement of crystal objects due to transportation between microscopes.

PTP1B

UVF  Visible

METHODS FOR VISUALIZING CRYSTALS AND DISTINGUISHING CRYSTALS FROM OTHER MATTER WITHIN A BIOLOGICAL SAMPLE

The subject application is a continuation-in-part of pending U.S. patent application Ser. No. 10/832,748, filed on Apr. 27, 2004, herein incorporated in its entirety by reference.

BACKGROUND OF THE INVENTION

1. Technical Field

The subject invention relates to methods of observing protein crystals so as to distinguish such crystals from other materials within a test sample as well as to obtain a vivid and precise image of the protein crystalline material of interest.

2. Background Information

In scientific studies of the three-dimensional atomic structure of biological macromolecules, X-ray or other diffraction experiments are extensively and widely used. These methods require the regular array of replicate molecules presented by highly ordered crystalline states of matter. Often great effort is expended in finding or screening conditions suitable for forming, growing, and harvesting crystals of sufficient size and quality. Further, the structure and mode of binding of a ligand to its target are often derived from the data.

In the area of drug discovery research, many ligand structures are desired in order to optimize and guide iterative medicinal chemistry synthesis toward achieving the binding properties desired for a drug molecule. For pharmacological reasons, the target of many drugs is a protein molecule so a large fraction of X-ray crystallography research in drug discovery is performed on crystals of proteins (see Anderson et al., *Chem. Biol.* 10(9):787-97 (2003)). Interest and effort are increasing in the attempt to obtain structures of membrane-bound proteins such as cell receptors.

Lacking direct molecular control to build a crystal at the molecular level, scientists rely on large numbers of tests to find conditions where a concentration or other gradient, such as those induced by vapor diffusion, will allow or drive a crystal to form. Such a crystal, or at least a zone within the crystal, must be solid, large enough, and relatively free of defects for it to yield good X-ray diffraction data. If a particular crystal growth test is successful, the location, size or form of the crystal is unpredictable (see McPherson et al., *Structure* 3:759-68 (1995)). Multiple crystals can form as well causing additional difficulties. Steps of adding crystal seeds or presenting crystal-inducing surfaces have been used but are not universally applicable.

Unfortunately, in the solutions and solution mixtures used to promote the formation or growth of a crystalline phase of a target macromolecule, very often other undesired solid material can form whose composition is unknown and can obscure or distract in the identification of crystals actually worthy of X-ray diffraction experiments (see McPherson, A., Preparation and Analysis of Protein Crystals, 1982, Krieger Publishing Co., Inc., Malabar, Fla., pp. 179-180). Salt, detergent, polyethylene glycol, lipids or other excipients can also form crystals (or precipitate). Some of these can have similar morphology or outwardly resemble the desired crystals. Amorphous precipitates, liquid phase separations or skins on droplets are also occasionally observed. These may be composed of, or include, protein to some degree. Therefore, with such a plethora of possibilities it becomes important to be able to monitor and identify protein crystals in such crystallization attempts, usually performed in multiple sites or chambers.

At the present time, 96-chamber plastic plates have gained popularity as a sample format for screening large numbers of crystallization trials. Using these plates, in the vapor diffusion method of crystallization, a protein solution is confined as a sitting droplet by a well. Crystals are relatively small and can form at various locations within the well. A basin below contains the reservoir liquid that slowly adjusts through vapor diffusion the protein solution droplet's concentration in crystallizing agents. Another well-known format used extensively in the past is to hang a droplet from a cover over the reservoir.

Existing methods of microscopy of materials have limitations in their application to these types of samples. Phase, birefringence, retardance, crossed-polarizer or other contrast methods using visible light and, for example, exploiting the difference in index of refraction between protein crystal and solution, may not be conclusive enough alone to allow convenient or rapid scoring of crystallization attempts. Cross polarization for example, uses the anisotropic nature of crystalline materials to refract light and produce birefringence. Birefringent crystals appear as rainbow colored objects against a dark background. Crystals with little structural anisotropy may not be birefringent, for example, the bacterial cell division protein FtsZ (Löwe, J. et al., *Nature* 391(6663): 203-6 (1998)). If the isotropic nature of protein crystals that grow from a given sample is not known before screening, the use of birefringence will result in some missed hits. Many organic and inorganic materials present in crystallization screens can also form birefringent crystals that result in false positives.

Absorbance or transmitted light microscopy in the UV for this purpose is difficult in most crystal growth formats. For spectral information, crystals are generally removed and mounted in instruments for examination (Bourgeois, D. et al., *J. Appl. Cryst.* 35:319 (2002)).

Chemical modification of a protein prior to crystallization (such as attaching a fluorescent probe, see Sumida, J. et al., *J. Cryst. Growth* 232:308-316 (2001)) in order to more easily visualize its crystals when they form is usually undesirable for the risk of denaturing the protein, or altering its biochemical, e.g. compound-binding, properties in subtle or major ways. The crystallization behavior of the protein may also be unpredictably altered.

In order to recognize protein crystals, dyes can be added to a crystallization well after crystals form that adsorb into or stain protein specifically [www.hamptonresearch.com; http://www.hamptonresearch.com/hrproducts/4710.html]; however, such a process is time consuming and invasive, as it can modify crystals substantially and can alter or abrogate the binding of any drug-like compound under study, and thus is limited to cases where the crystals need not be harvested.

In view of the above, a definite need exists for non-invasive methods that allow one to inspect crystals such that one can distinguish them from other materials in a sample as well as to visualize the crystals precisely.

All patents and publications referred to herein are hereby incorporated in their entirety by reference.

SUMMARY OF THE INVENTION

The subject invention encompasses a method of distinguishing a crystal within a biological sample. This method comprises the steps of: a) exposing the biological sample to ultraviolet radiation; b) detecting radiation emission from the exposed biological sample; and c) analyzing the emission of step b) and distinguishing the crystal within the sample by results of the analysis. In particular, in connection with step c), one may analyze the emission of step b) in connection with its intensity, spectral, temporal or other photonic properties. One then distinguishes the crystal by determining whether, over the spatial extent, if any, of the biological sample, the emission has changed somewhere relative to a solution or sample where no crystal is present (such as prior to addition or presence of a crystallization-inducing excipient or immediately after but before a crystal could form), or whether within the boundaries of the biological sample, the variations in the emission properties occur which are greater than those of a solution or sample in which no crystal is present. In this method, the ultraviolet radiation utilized preferably has a wavelength of less than 351 nm, more preferably, between 140 nm and 320 nm and, most preferably between 260 nm and 300 nm. (Both endpoints within each range are also included.) The biological material may be, for example, a protein, a peptide, a cofactor, a nucleic acid, or a mixture of any one of more of these entities. (An artificial membrane may also be analyzed.) Further, the radiation emission may result from excitement of luminescence of the crystal by the UV radiation of step a). The luminescence may be intrinsic to the crystal and may be fluorescence (e.g., polarized fluorescence) or phosphorescence.

Further, the present invention includes an additional method of distinguishing a crystal from other matter within a biological sample. This method comprises the steps of: a) exposing the biological sample to UV radiation; b) detecting scattered photons from the exposed biological sample; and c) analyzing the scattered photons of step b) by determining whether 1) the scattered photons of the biological sample have changed in comparison to a sample comprising no crystal or 2) whether variations in the scattered photons of the biological sample are greater than the sample comprising no crystal, the change or variations allowing the crystal to be distinguished from the other matter within the biological sample. Thus, the method described above and as well as this method follow virtually the sample protocol in connection with step c). The scattered photons may be of the Brillouin type or be Raman shifted from an incident wavelength of preferably between 140 nm and 350 nm and, more preferably, between 200 nm and 270 nm. The biological material may be as described above in connection with the other method.

Additionally, the present invention encompasses a method of determining whether a ligand within a crystal has bound to a receptor. This method comprises the steps of: a) measuring emission of a crystal, comprising a receptor to the ligand, prior to addition of the ligand; b) adding the ligand to the crystal; c) measuring emission of the crystal subsequent to addition of the ligand; and d) determining whether the ligand has bound to the receptor by comparing the emission of step a) with the emission of step c), a difference in emission between step a) and step c) indicating binding of the ligand to the receptor. The emission may be, luminescence, for example, the result of fluorescence or phosphorescence. The scattered light may be Raman shifted.

The present invention also encompasses a method of determining presence of a compound within a "distinguished" crystal. (In the context of the present invention, the term "distinguished" means a crystal which has been identified, separated or differentiated (e.g., via visualization or other means) from the other matter within a biological sample, based upon one of the methods described herein.) This method comprises the steps of: a) determining reference UV-excited emission or UV scattered light spectrum of the compound for: 1) free compound or 2) free compound and compound bound to a receptor (e.g., in solution); b) measuring the ultraviolet (UV)-excited emission or scattered UV light spectrum of a test crystal suspected of containing the compound bound to the receptor; c) comparing the emission or spectrum of step b) with the reference emission, spectrum or spectra of step a), comparable emission or spectrum of the compound bound to receptor or deviation from compound free in solution indicating presence of the compound within the test crystal, and comparable spectrum with the compound free in solution or deviation from compound bound to protein indicating absence of the compound within the test crystal. (Methods of determining comparable or corresponding spectrum are known to those of ordinary skill in the art. (See e.g., Handbook of Near-Infrared Analysis, eds., Burns et al., Marcel Dekker; see also Martans et al., Multivariate Calibration, Wiley; Geladi et al., Multivariate Image Analysis, Wiley; and Lewis et al., *Spectroscopy* 19(4):26 (2004).)) Again, the emission may be luminescence, for example, fluorescence or phosphorescence, as is possible in connection with all of the methods described herein. Further, the scattered light may be Raman shifted, for example.

Additionally, the present invention includes another method of determining whether, within a distinguished crystal, a ligand has bound to a receptor. This method comprises the steps of: a) measuring UV-excited emission or UV scattered light of a first crystal and a second crystal, the first crystal comprising the receptor to the ligand and the second crystal comprising the test crystal, the test crystal being suspected of comprising the ligand bound to the receptor; and b) determining whether the ligand has bound to the receptor in the second crystal (i.e., the test crystal) by comparing the emission of the first crystal and the second crystal (i.e., the test crystal) of step a), a difference in emission indicating binding of the ligand to the receptor of the second crystal. The emission may be, for example, luminescence such as fluorescence or phosphorescence. Further, the scattered light may be Raman shifted.

DETAILED DESCRIPTION OF THE INVENTION

The present invention relates to methods of distinguishing, locating, isolating, differentiating, and/or analyzing crystals of biological macromolecules such as proteins, peptides, cofactors, nucleic acids, cell membranes, or mixed crystals thereof. Such methods may additionally be carried out on such crystals that also contain test compounds or molecules whose structure may result in their use as a potential therapeutic. More specifically, the methods are accomplished by detecting intrinsic fluorescence, phosphorescence or other luminescence excited by UV radiation, or Raman or Brillouin scattering of UV radiation. The crystals are those used for, prior to, or in conjunction with subsequent or related X-ray diffraction experiments for three-dimensional atomic structure determination.

Figure 14:
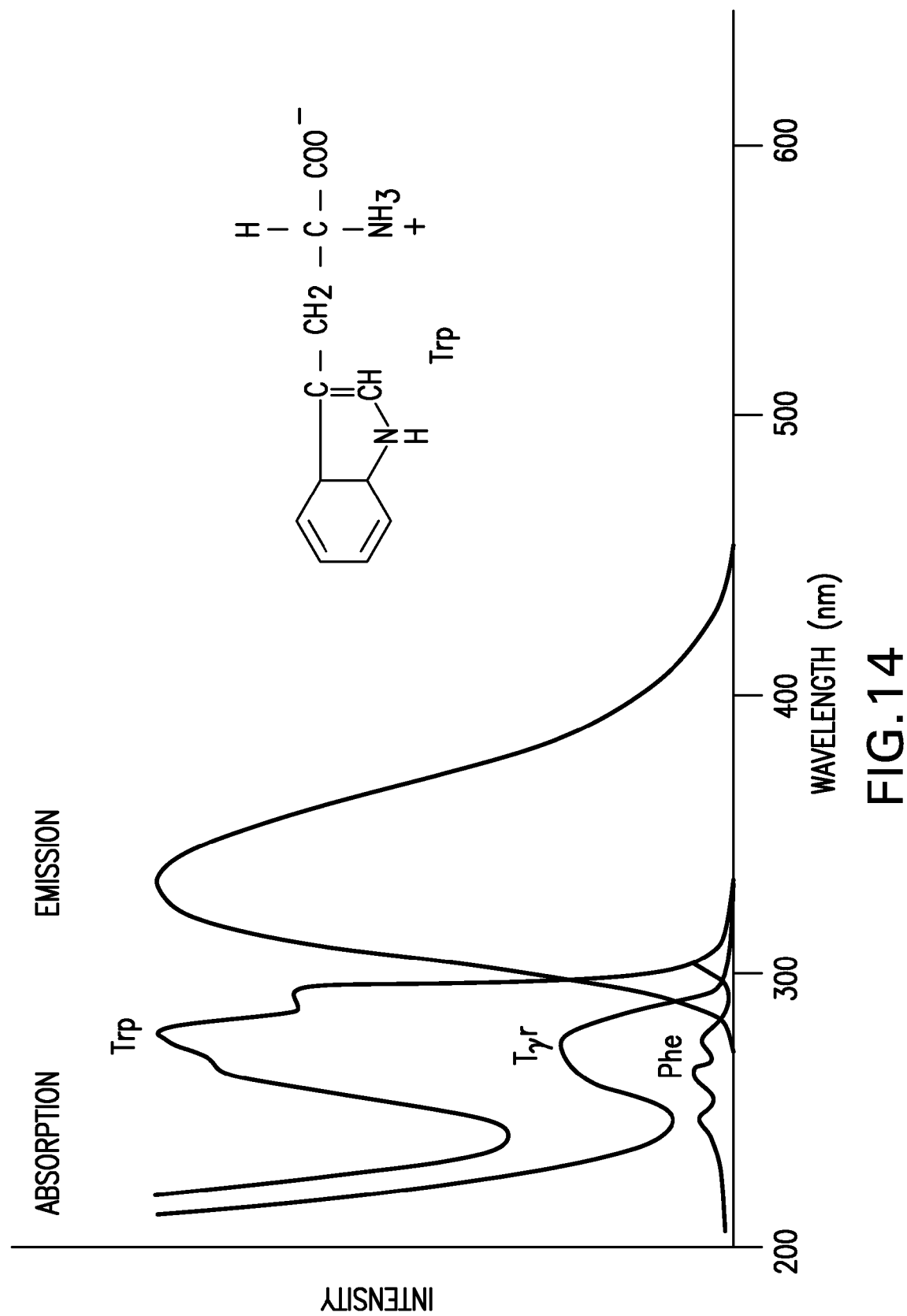
FIG. 14 plots fluorescence excitation spectra for the aromatic side-chain amino acids phenylalanine, tyrosine and tryptophan shown with the fluorescence emission spectra for tryptophan (Lakowicz, Principles of Fluorescence Spectroscopy, 2cd ed., p. 16 (1999)).

One of the methods of the present invention comprises the steps of: 1) shining UV electromagnetic radiation from a light source onto the sample; 2) detecting the response radiation emission or scattered photons; and 3) finding or otherwise identifying the desired crystals by analyzing the data covering the field of view encompassed by the area where crystals are allowed to or can grow. In particular, the first step of the method is to illuminate the sample with UV radiation at a wavelength, or through a band, where some radiation has a wavelength less than 351 nm and, more preferably, for the case of exciting protein luminescence, in the range of between 140 nm and 320 nm, and most preferably in the range of between 260 nm and 300 nm. (The recited endpoints are also considered to fall within the scope of the range.) The light source may be continuously emitting, flashing, or modulated. Examples of suitable light sources include deuterium lamps, short-arc lamps and lasers. Any optical components used to direct, collimate, reflect, focus, or which simply pass the excitation light onto the sample, must transmit (or reflect) the UV excitation wavelength in the range of less than 351 nm. For example, the range of approximately 260-320 nm includes the upper wavelength band of absorption of the fluorescent amino acids tyrosine and tryptophan (see FIG. 14; see also Joseph R. Lakowicz, Principles of Fluorescence Spectroscopy, 1st edition, New York, Plenum Press (1983), p. 343 and Eugene A. Permyakov, Luminescent Spectroscopy of Proteins, CRC Press, Boca Raton, (1993)).

An additional strong absorption band at higher energy for tryptophan and tyrosine may allow luminescence excitation at lower wavelengths (e.g., <260 nm) with the present methods as long as sufficient transmission of excitation light through and no accidental, overwhelming background fluorescence or other interference from materials and optics is caused. As known from the general knowledge in the field of fluorescence spectroscopy, the fluorescence emission spectrum remains the same due to molecular radiationless relaxation before emission of photons (Lakowicz, ibid., p. 4). Phenylalanine excites quite well at wavelengths below 220 nm. Certain buffer constituents may interfere with lower excitation wavelengths by their (or a contaminant's) intrinsic fluorescence as a background, reducing contrast, and crystallization buffer solutions may therefore need to be checked beforehand, or more often, if such shorter excitation wavelengths are employed. If nothing else occurs, the presence of some water vapor and at least nitrogen in the atmosphere surrounding the optics and solutions of the experiment surely will limit luminescence excitation wavelengths to be greater than around 140 nm.

Control of the dose of excitation radiation may be necessary to prevent sample damage, and also provides a means of confirming genuine fluorescence specific to the desired crystal. Some eventual fading of fluorescence is expected, but accidental pick-up of reflections or other stray light should remain relatively constant.

In this method, the glass or anti-reflection coating used in common objective lenses or other focusing lenses is unsuitable. UV transmitting lenses from fused silica ("quartz") are available. However, many, in fact, most compound microscopes for fluorescent biological samples that are commercially available contain multiple glass elements and do not allow excitation in this range of ultraviolet wavelengths (<351 nm). Biological fluorescence microscopy refers today mostly to work with excitation in the visible range, or near ultraviolet range (commonly at 365 nm (see Walter C. McCrone, Lucy B. McCrone, John Gustav Delly, Polarized Light Microscopy, McCrone Research Institute, Chicago, Ill. (1985)), or 351 nm for confocal UV laser scanning microscopy) of the electromagnetic spectrum and often involves use of purpose-specific dyes or visibly fluorescent proteins (e.g., green fluorescent protein, GFP), incorporated or conjugated to proteins or other molecules in some way, rather than the intrinsic UV-excited fluorescence of proteins, nucleic acids, NADH, or other common biological constituents.

Figure 13:
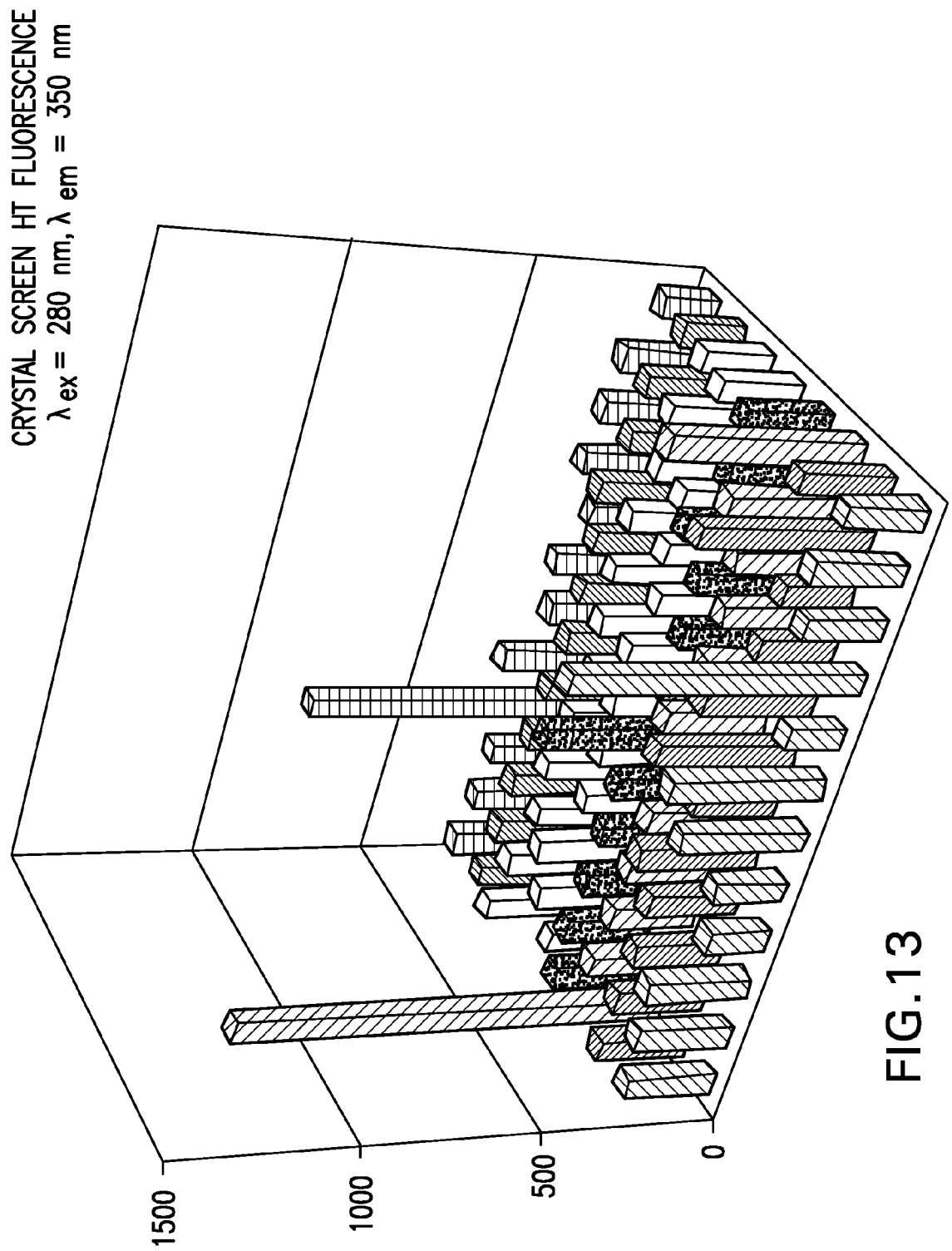
FIG. 13 graphs data for background fluorescence from a collection of buffers used in one of a number of commercial crystallization screens tested for any background fluorescence.

In the methods of the present invention, covers of the sample containers used to prevent evaporation of the solution are usually made of materials such as glass or plastic. However, other materials may also be utilized. These thin sheets or coverslips can pass the excitation light to a sufficient degree to allow the present methods of the invention to work successfully. Plastics used in the sample container floor or its frame do not fluoresce much under conditions used for detecting protein fluorescence. Also, buffers and excipients used to favor the formation of protein crystals fluoresce only to a limited degree, producing less than 30% background with respect to the level expected for typical protein fluorescence. In one 96-position screen that is used as a sparse matrix for high throughput, only three conditions stood out to that degree (see FIG. 13). PEG MMEs (polyethylene glycol monomethyl ethers) were contained in two of these (Jancarik et al., *Cryst.* 24:409-411 (1991)). Again, this fluorescence is still small compared to that of protein in crystals.

Figure 1:
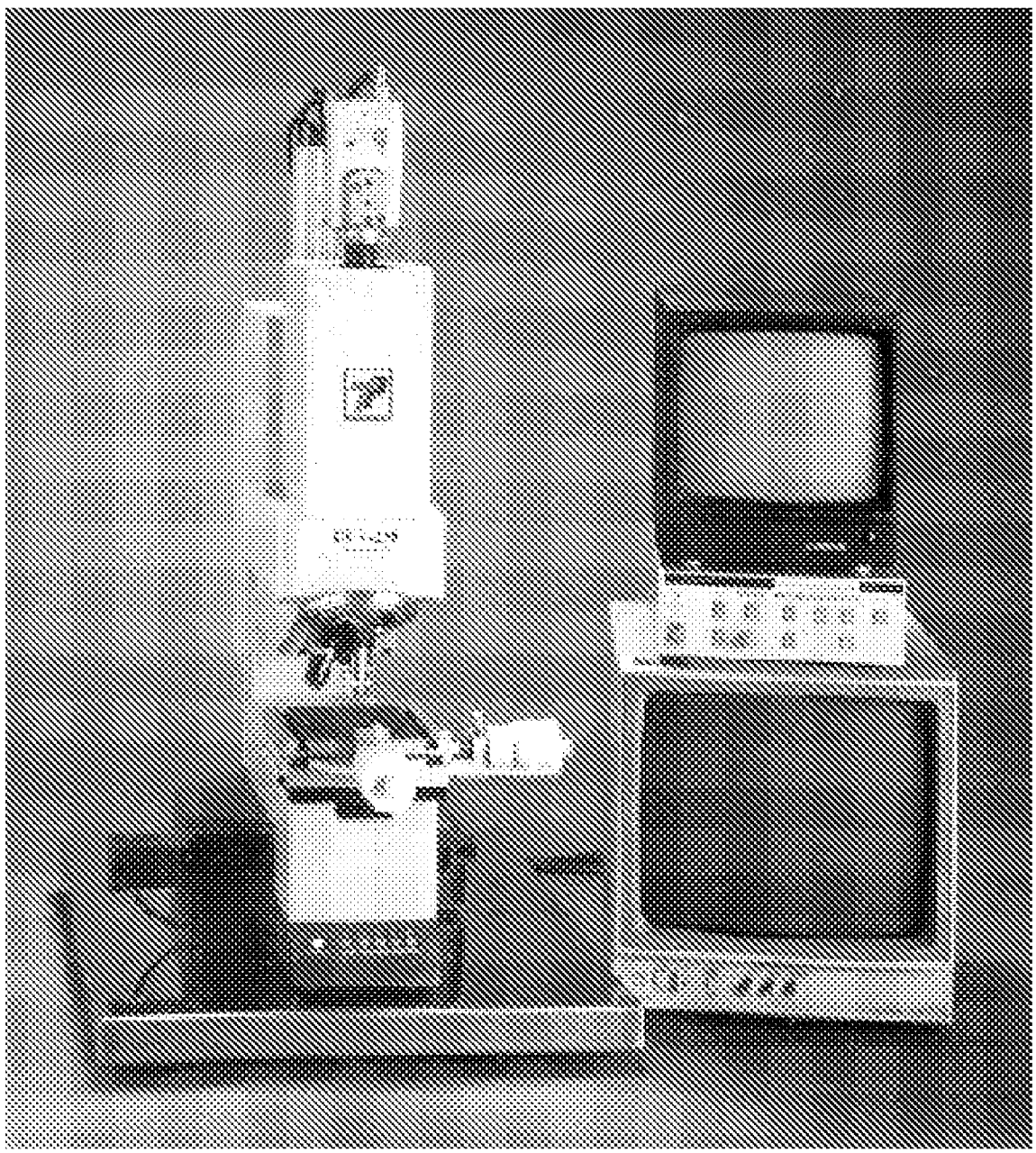
FIG. 1 illustrates the UV epifluorescence microscope used in the methods of the present invention.
Figure 21:
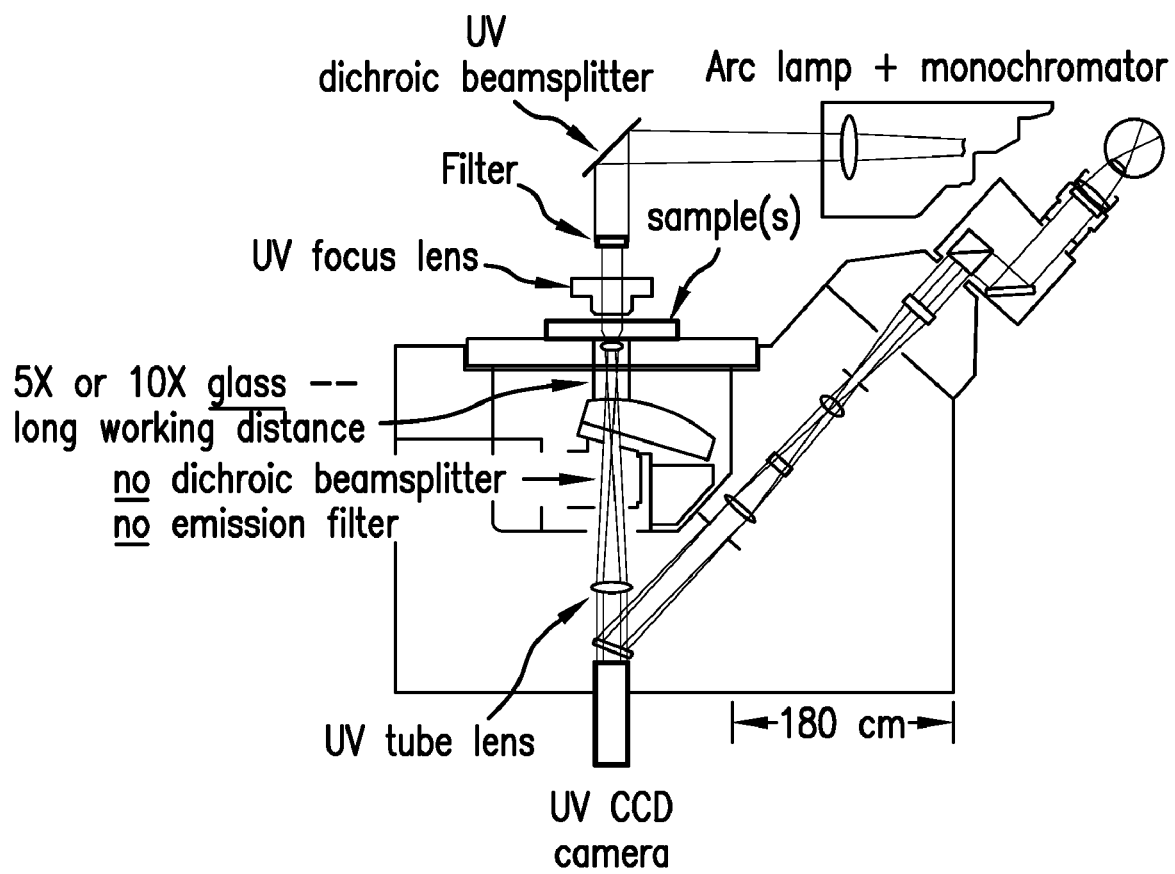
FIG. 21 illustrates another straight-through optical configuration, using a modified inverted microscope.
Figure 22:
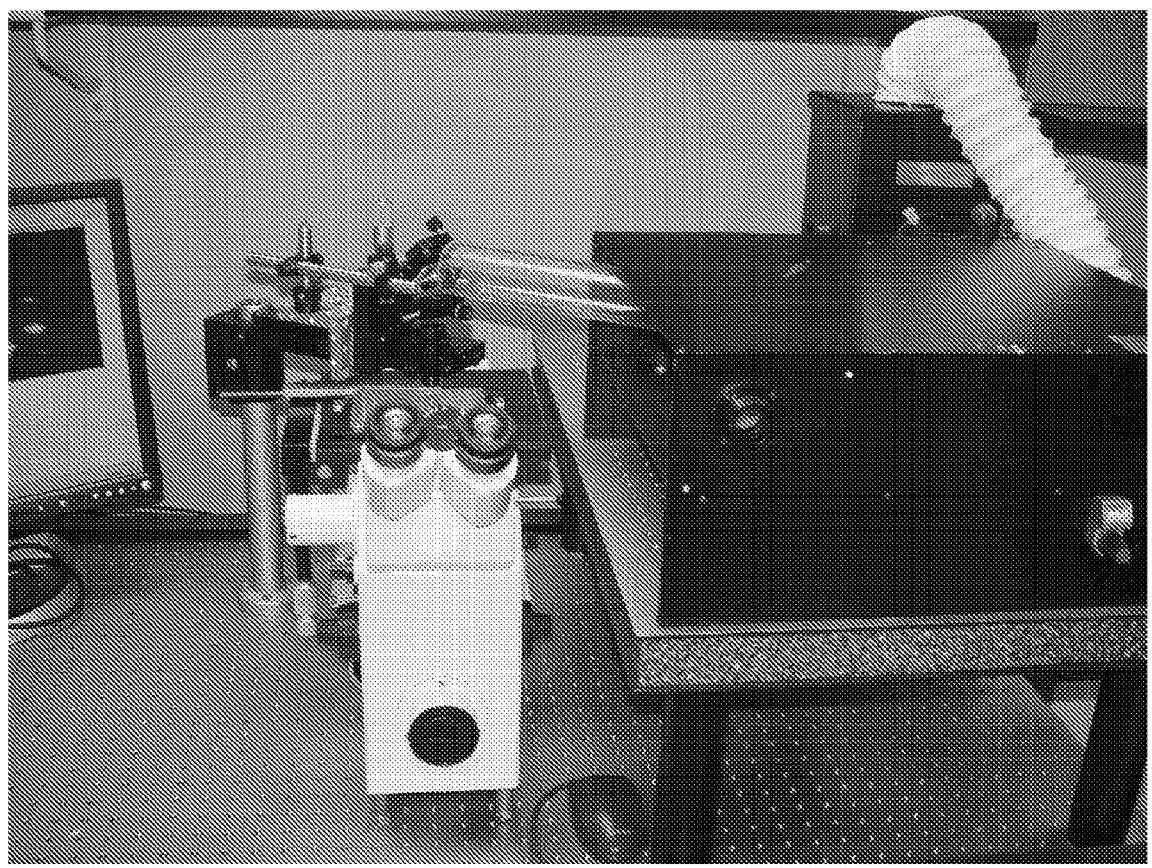
FIG. 22 includes a photograph of the apparatus illustrated in FIG. 21.

The second step of the present methods is the detection of the sample response at a longer wavelength than that of the excitation (or conceivably, at a shorter wavelength, in particular, for the case of anti-Stokes Raman scattering). These luminescence or scattered light emissions are usually isotropic in space at least to some degree so collection geometry is often mostly dictated by the sample format, and, it was demonstrated, for example, that epifluorescence through the objective lens above the sample works well (see FIGS. 1 and 2). A straight-through configuration with excitation through the top and observation from the bottom is also feasible and was demonstrated (see FIGS. 3 and 4). Also, a straight-through geometry was implemented using a modified inverted microscope (C. Zeiss, Jena, Germany)(see FIGS. 21 and 22). In particular, a fused silica lens was retrofitted as the tube lens by the manufacturer, which helped reduce attenuation of fluorescence on the short wavelength side of the emission spectrum. The glass of the achromatic objective lens (Leica HC PL Fluotar) was able to block all excitation light from reaching the detector while imaging the emission. This rendition has an advantage of convenient viewing of the sample by eye through the eyepiece. The longer wavelength tail of a protein's emission spectrum extends into the visible, and the dark adapted human eye can see the blue glow of the fluorescence in some cases. The eyepiece has a larger field of view than the CCD camera.

Detection can be continuous, synchronous, gain-modulated, gated, or delayed relative to excitation events. Suitable detectors include, for example, CCD (charged coupled device) linear or two-dimensional arrays, photodiodes and photodiode arrays, avalanche photodiodes, photo(electron) multiplier tubes (PMT), multiple anode PMT's, microchannel plates, and microchannel plate intensified CCD detectors. Typically, it is necessary to use an optical spectral or possibly also a polarization filter to block transmitted, reflected, scattered or otherwise back- or forward-coupled excitation light from impinging on the detector. When protein fluorescence is viewed, the band of emission extends from 320 to 400 nm (see FIG. 14). Phosphorescence extends yet farther into the visible. Raman scattering is found in bands shifted in terms of energy from the incident light (typically a laser line) and bands specific to protein vibrational group frequencies are known, for example, amide I at approximately 1650 $cm^{-1}$.

The use of additional wavelength discriminating optical elements may also be desirable in order to select part of the emission. For example, the spectral characteristics of protein intrinsic fluorescence emission indicate the immediate molecular electronic environment of the fluorescent amino acids. An additional benefit of the methods of the present invention is to allow analysis of the emission spectrum for a number of features. A correlation of protein crystal's emission spectral characteristics with its X-ray diffraction has been shown. (Asanov et al., *Journal of Crystal Growth* 232: 603 (2001)). Furthermore, if a ligand binds, there can be a consequent direct proximal, semi-proximal or allosteric electronic environment change for the fluorescent amino acids, and in any case there is the possibility of a spectral or quantum yield change due to energy or photon transfer, e.g. Förster Resonance Energy Transfer (FRET). By monitoring emission intensity at particular wavelengths before and after, with or without compound present, this effect may be used as a convenient means to verify the presence and binding of a ligand in the crystal prior to an X-ray diffraction experiment. Alignment of fluorophores in a crystal can bring about distinctive orientational and polarization effects, as observed for GFP in the visible range (Inoué et al., *Proc. Natl. Acad. Sci., USA* 99:4272 (2002)). Thus, the utility of monitoring these effects for indication of quality and prediction of degree of diffraction for the planned X-ray crystallography may be envisioned. Temporal discrimination (i.e., delay of the detection time window relative to excitation) may also be desirable. For example, measuring or imaging fluorescence lifetime (FLIM) may allow a protein-specific signature to be detected independent of overall intensity level. Phosphorescence is considerably delayed relative to fluorescence and can also provide a unique chemical signature.

Additionally, drug or drug-like test compounds themselves can show interesting changes in their own fluorescence upon binding, so monitoring their specific emission excited at appropriate wavelengths may be useful (see, for example, urokinase naphthamadine inhibitor series; International Patent Application Publication No. WO 99/05096, unpublished results). Furthermore, Raman spectroscopy in the visible range has been used to show binding of compounds (Dong et al., *Biochemistry* 40(33):9751-9757 (2001)), and in the UV range, a resonance enhancement due to an incident beam's wavelength being near the absorption bands will deliver a sensitivity advantage.

The resonance enhancement of protein Raman bands wavelengths are in the range of 200-260 nm (Sanford Asher, *Analytical Chemistry* 65(4), 201 A (1993)), but other incident wavelengths may be possible as long as the desired Raman signature does not fall in a range where considerable fluorescence or other luminescence is present. Brillouin scattering, with characteristic shifts lower in frequency magnitude than Raman, results from intermolecular vibrations such as those of lattice modes of a crystal (a.k.a. phonons) and could correlate with crystal quality and suitability for X-ray diffraction experiments.

The third step of the methods of the present invention is the accommodation of the physical format used to grow or confine crystals by collecting the emission response in such a way as to take one or more readings, for example, to capture an image of the sample optically or by moving or scanning the sample (or excitation light) through its extent point-by-point, by sections, or in a raster pattern, or in some other way, possibly but not necessarily processing these data so as to form an image. It may be that line or pattern scans which collect a subset of the image are sufficient for rapid scoring of a well for presence or absence of crystals. Within these data, bright objects will correspond to the desired crystals. This step allows the methods to be used in situ, that is, without harvesting or displacing any crystal, unlike in a UV intrinsic fluorescence method of prior art ((Asanov et al., *Journal of Crystal Growth* 232:603 (2001)).

In some methods of crystallization where attractive zones or even simple solution confinement force or induce crystals to form at specific locations on a surface, sensing an increase in protein fluorescence near the surface is indicative of the formation of the crystal because a crystal's protein concentration is always higher than that of the corresponding mother solution. For this special case of detecting crystal formation, our method of detecting crystals by a protein's intrinsic luminescence can be employed, if necessary, with only a single-element detector and fixed confocal detection optics because there is no requirement for capturing an image or multiple readings at different points in the sample.

Figure 2:
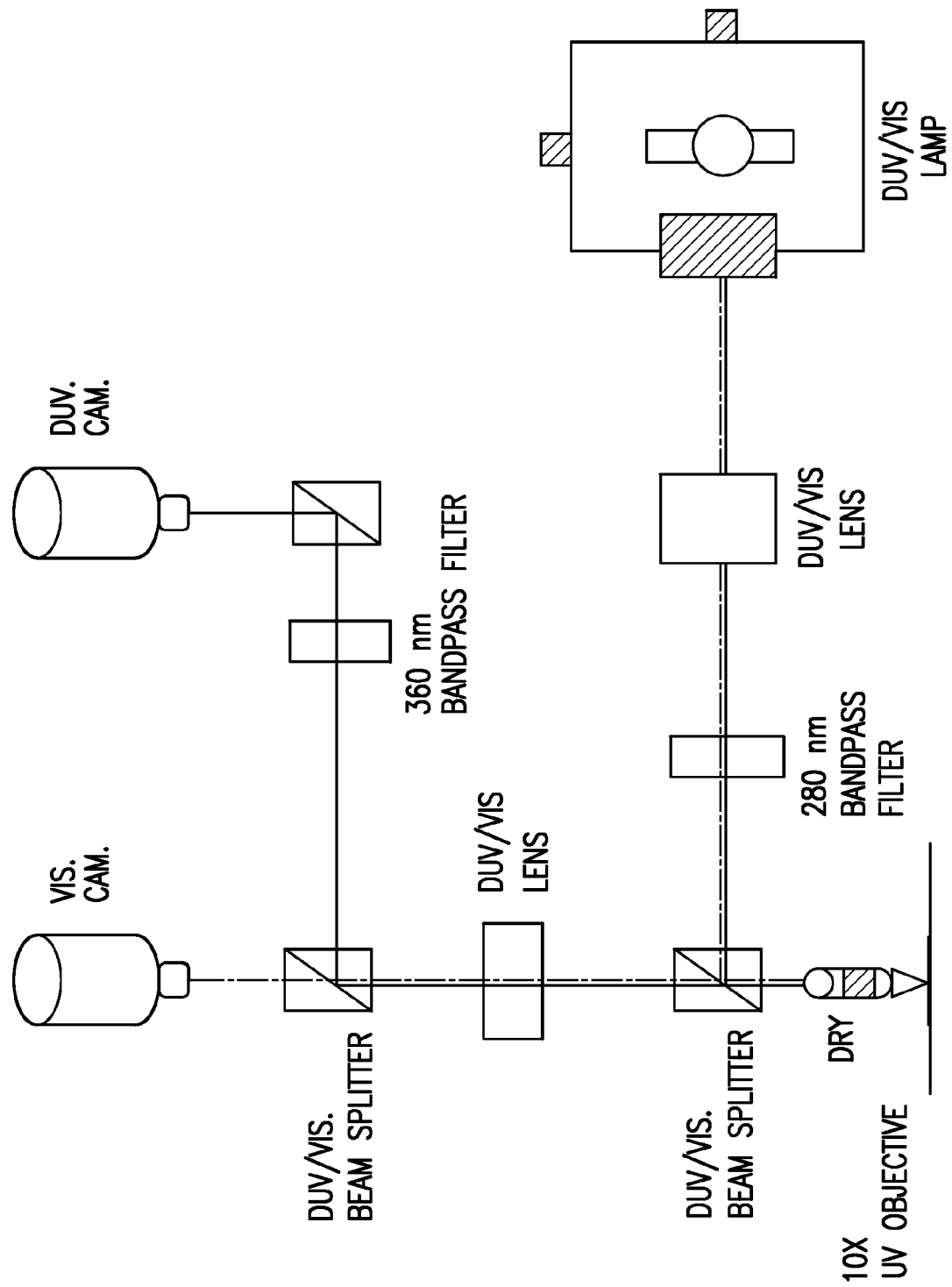
FIG. 2 represents a block diagram of the UV epifluorescence microscope configuration.
Figure 5:
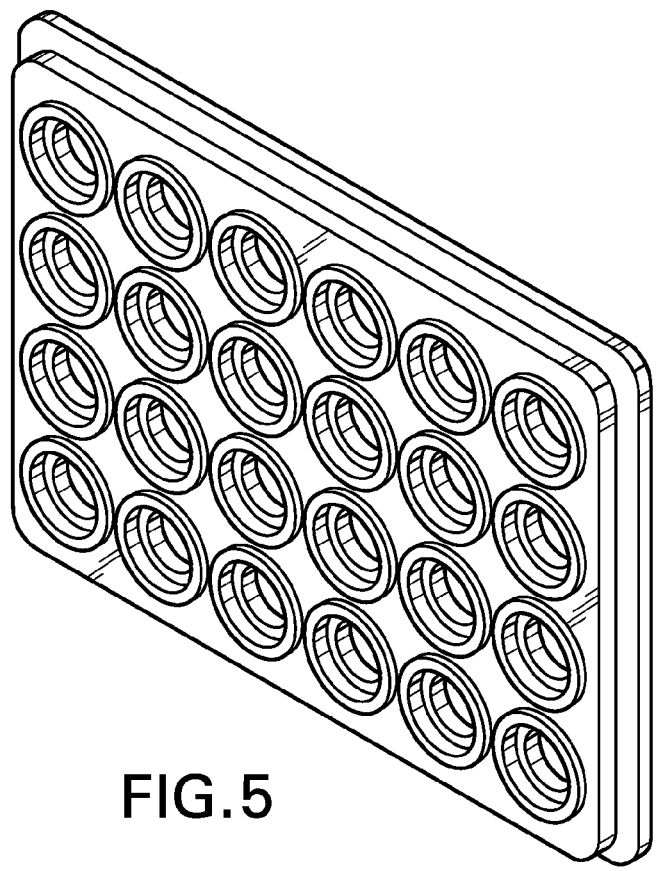
FIG. 5 illustrates a Linbro plate for hanging drop crystal growth.
Figure 6:
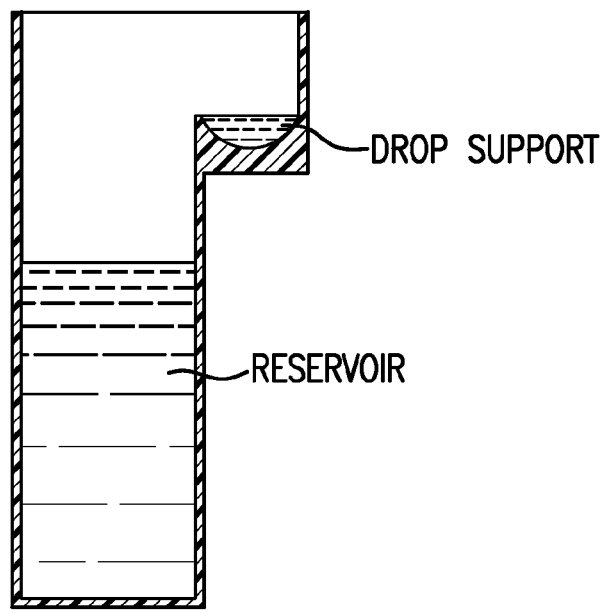
FIG. 6 diagrams one well of a high throughput vapor diffusion (96-well) crystallization plate.
Figure 7:
FIG. 7 illustrates glucose isomerase crystals visualized by UV fluorescence imaging in epifluorescence.

One embodiment of the present invention involves the use of a 2-D CCD detector to collect the UV-excited fluorescence image of a significant fraction of the crystal growth area, e.g., "the well" (see FIGS. 5 & 6). Using this method, protein crystals are recognizable in a wide-field epifluorescence or straight-through fluorescence image by their intrinsic fluorescence emission which is much brighter than that from residual protein in surrounding solution (e.g., see FIG. 7). For this particular test, as shown in FIG. 2, a 20 nm band centered at 280 nm was excited and emission was collected in a 40 nm band centered at 360 nm. Furthermore, under these conditions, salt crystals, as predicted by considering their chemical constitution, did not produce any luminescence, and appeared as dark objects (see FIGS. 10 and 11).

By moving the focus, data can also be collected through the depth dimension of the protein solution droplet. It is well known that three-dimensional data can also be reconstructed using a confocal optical microscope rendition. Confocal imaging techniques include, for example, laser scanning, Nipkow spinning disk, and dual spinning disk.

Even crystals that have already been harvested, for example, suspended somewhere inside a drop confined by a nylon fiber loop, are small enough that they need still to be located and placed precisely using a goniometer relative to the X-ray source when they are mounted on a diffractometer, in order to maximize or optimize the diffraction intensity and pattern. Due to similar lack of optical contrast like that observed in the crystal's growth medium, this may be somewhat difficult to accomplish using visible light to illuminate the sample. In this case, the methods of the present invention and, in particular, the UV fluorescence imaging method may also be used, in lieu of and in preference to monitoring X-ray diffraction itself (Pohl et al., *Biophysical Journal* 86, 397-Pos, 2004)).

A further embodiment of the present invention involves the implementation of the UV fluorescence imaging as a part of an automated system that can collect, store, and analyze a multitude of images from multiple samples without human intervention. Such an automated system can collect multiple images of the same sample each using illumination from different parts of the spectrum, including but not limited to UV, visible, and IR, to aid in distinguishing protein crystals from other crystalline or crystal-like matter. Furthermore, these multiple images may be collected at many predetermined time intervals to further distinguish growing protein crystals from static particulate or other image artifacts that do not change smoothly over time. By analyzing each of the different images collected by the automated system for each sample each involving variations in illumination wavelength, focus, time, and the type of detection technology (fluorescence, scattering, absorption), the automated system achieves a higher accuracy for identifying protein crystals over automated systems that collect or analyze images using only one illuminating wavelength, focus, time, and type of detection technology because certain aspects of the protein crystal may be more prominent in one type of image over another.

In yet a further embodiment, the ensemble of different images of the same sample collected by the automated system can be analyzed together as an ensemble to reduce the detrimental effects on accuracy that any one poor image may have on the ability to distinguish between protein crystals and other crystalline or crystal-like matter.

The present invention may be illustrated by the use of the following non-limiting examples:

EXAMPLE I

Visualization of Glucose Isomerase Crystals in Hanging Drops with Epi-fluorescence Glucose isomerase crystals were grown with 10 mg/ml glucose isomerase in 0.9-2.9 M ammonium sulfate, 0.1 M HEPES pH 7.7, at 23° C. In particular, the crystals were grown in 24 well Linbro plates (Hampton Research, 34 Journey, Aliso Viejo, Calif. 92656-3317) (see FIG. 5) by the hanging drop method. A quartz coverslip was used to suspend the drop over the reservoir solution. The sample was imaged with epifluorescence. The sample was excited through the objective lens used to collect the emission and pass the image to the CCD detector. The fluorescence image is shown as FIG. 7. The bright rod-shaped objects are the protein crystals, and the image shows high contrast. These crystals are 100-200 µm in length. Variation in brightness from crystal to crystal are due to the different depth positions relative to the focal plane of the objective lens, or perhaps also to crystal orientation effects. These crystals were determined to be isotropic in such a way as to shown no birefringence with visible light.

EXAMPLE II

Figure 8:
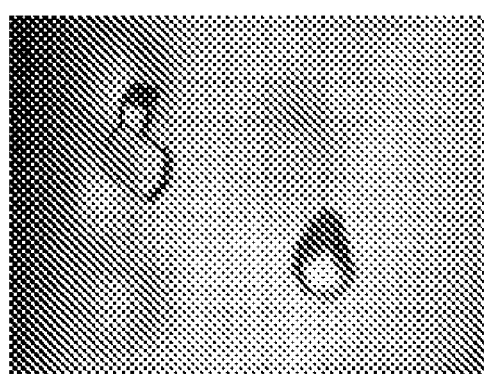
FIG. 8 shows crystals of chicken egg white lysozyme, viewed with visible light (for comparison) and with intrinsic UV-excited fluorescence using epifluorescence geometry.
Figure 8:
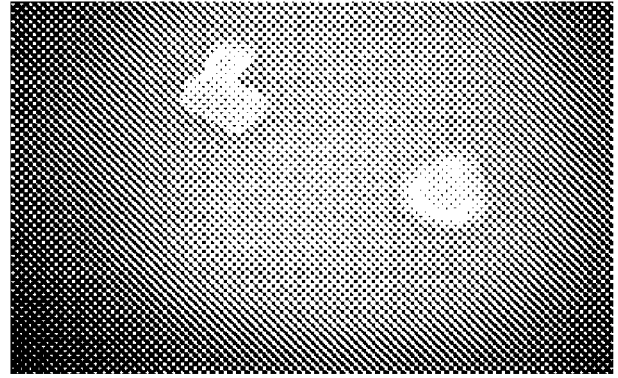

Visualization of Chicken Egg White Lysozyme Crystals in Sitting Drops with Epi-Fluorescence Lysozyme was grown from pH 4.5 NaOAc buffer, 50 mg/ml solution of protein mixed with equal volumes of 10% NaCl salt solution, same buffer. Reservoir contained 5% salt, same buffer. FIG. 8 shows a visible light image collected with an Olympus stereomicroscope Model SZX12 and an Olympus Model DP12 CCD camera. The sample was subsequently imaged with epifluorescence where the sample's intrinsic fluorescence was excited through the same objective lens used to collect the emission and pass the image to the CCD detector. In this case, a vapor diffusion 96-well high-throughput crystallization plate, covered in tape, contained the sample.

EXAMPLE III

Visualization of Glucose Isomerase Crystals in Sitting Drops

Figure 9A:
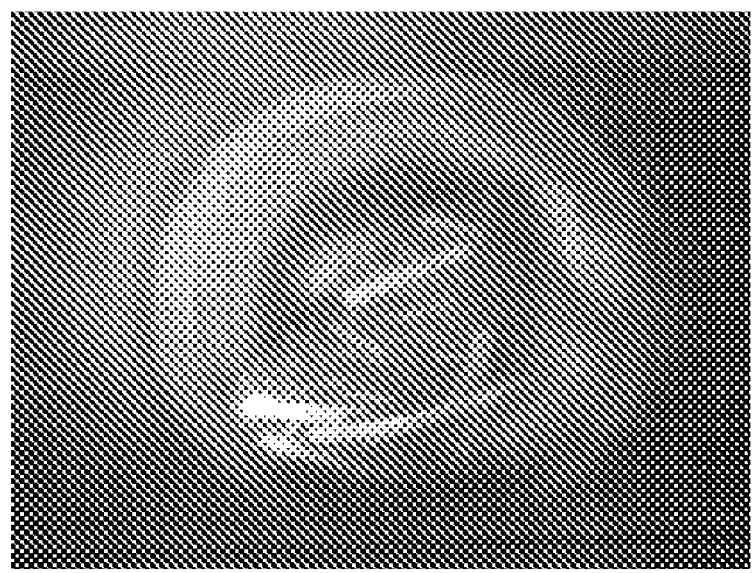
FIG. 9 shows glucose isomerase crystals viewed with visible light and visualized by UV fluorescence imaging in the straight-through geometry.
Figure 9A:
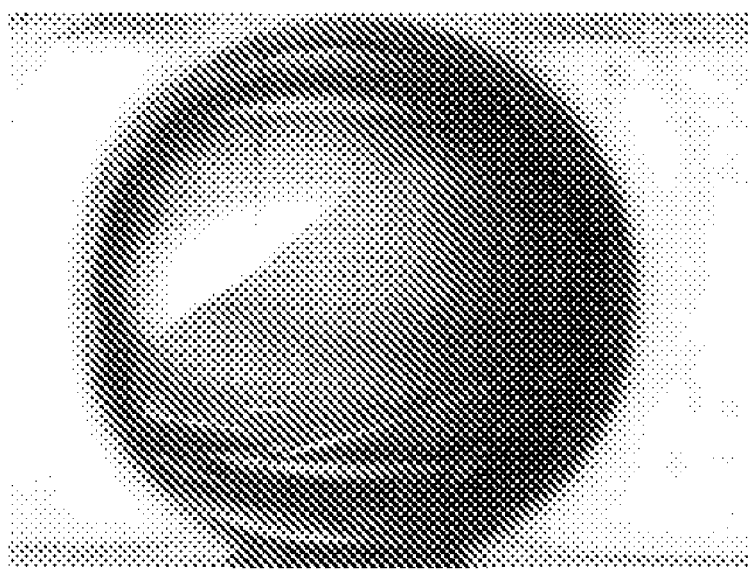
Figure 9B:
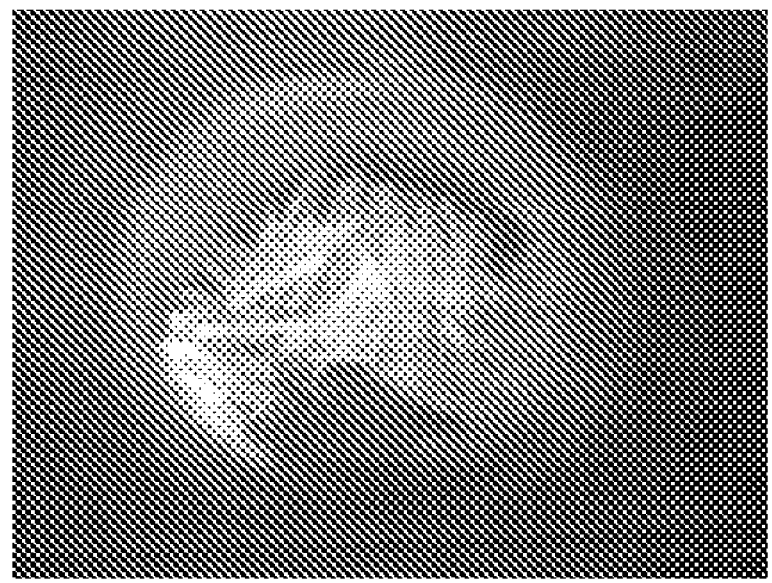
Figure 9B:
Figure 9C:
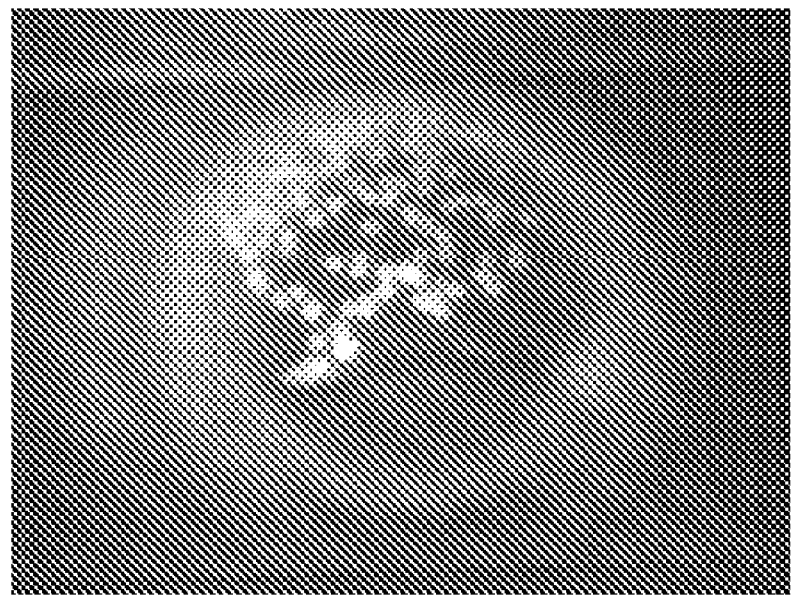
Figure 9C:
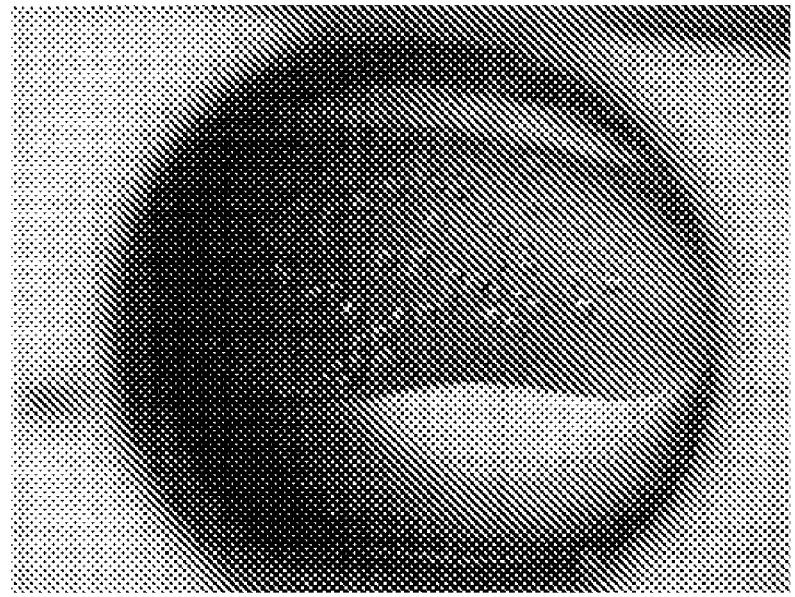
Figure 9D:
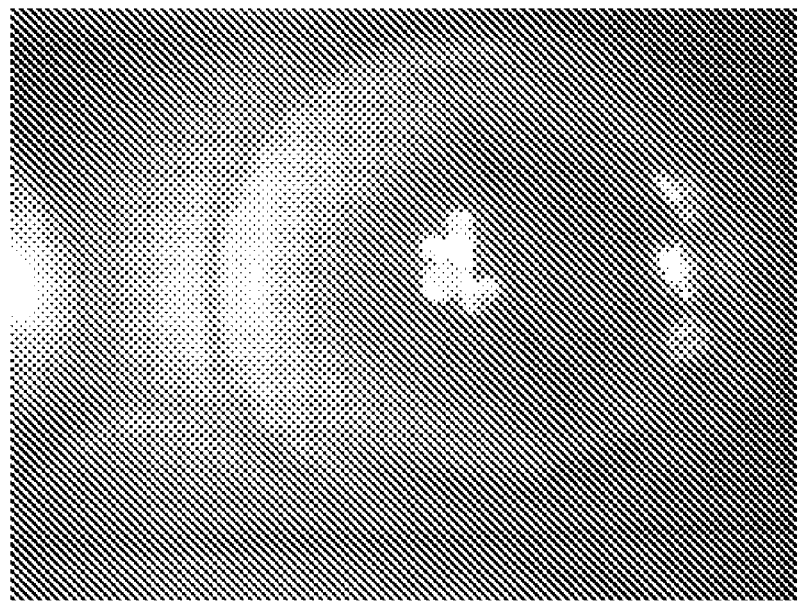
Figure 9D:
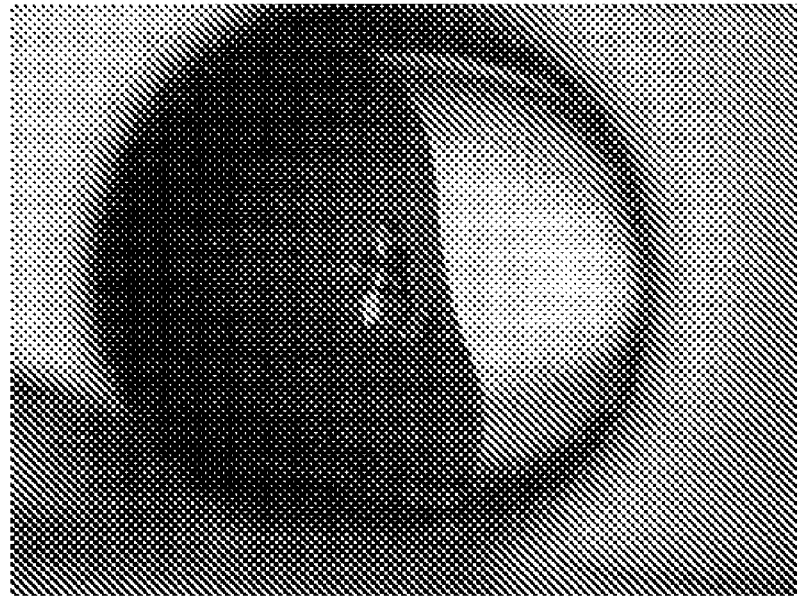

Glucose isomerase crystals were grown in sitting drops in a 96-well, high-throughput screening tray. Crystals were grown in 1.6 M ammonium sulfate, 0.1M Tris pH 8.0, 18 mg/ml glucose isomerase, 23° C. (FIG. 9a), 1.6 M ammonium sulfate, 0.1 M Bicine pH 9.0, 18 mg/ml glucose isomerase, 23° C. (FIG. 9b), 15% ethanol, 0.1 M HEPES pH 7.5, 0.2 M magnesium chloride, 23° C., 18 mg/ml glucose isomerase (FIG. 9c) and 20% PEG1000, 0.2 M $MgCl_2$, 0.1 M Na cacodylate pH 6.5, 23° C., 18 mg/ml glucose isomerase (FIG. 9d).

Figure 3:
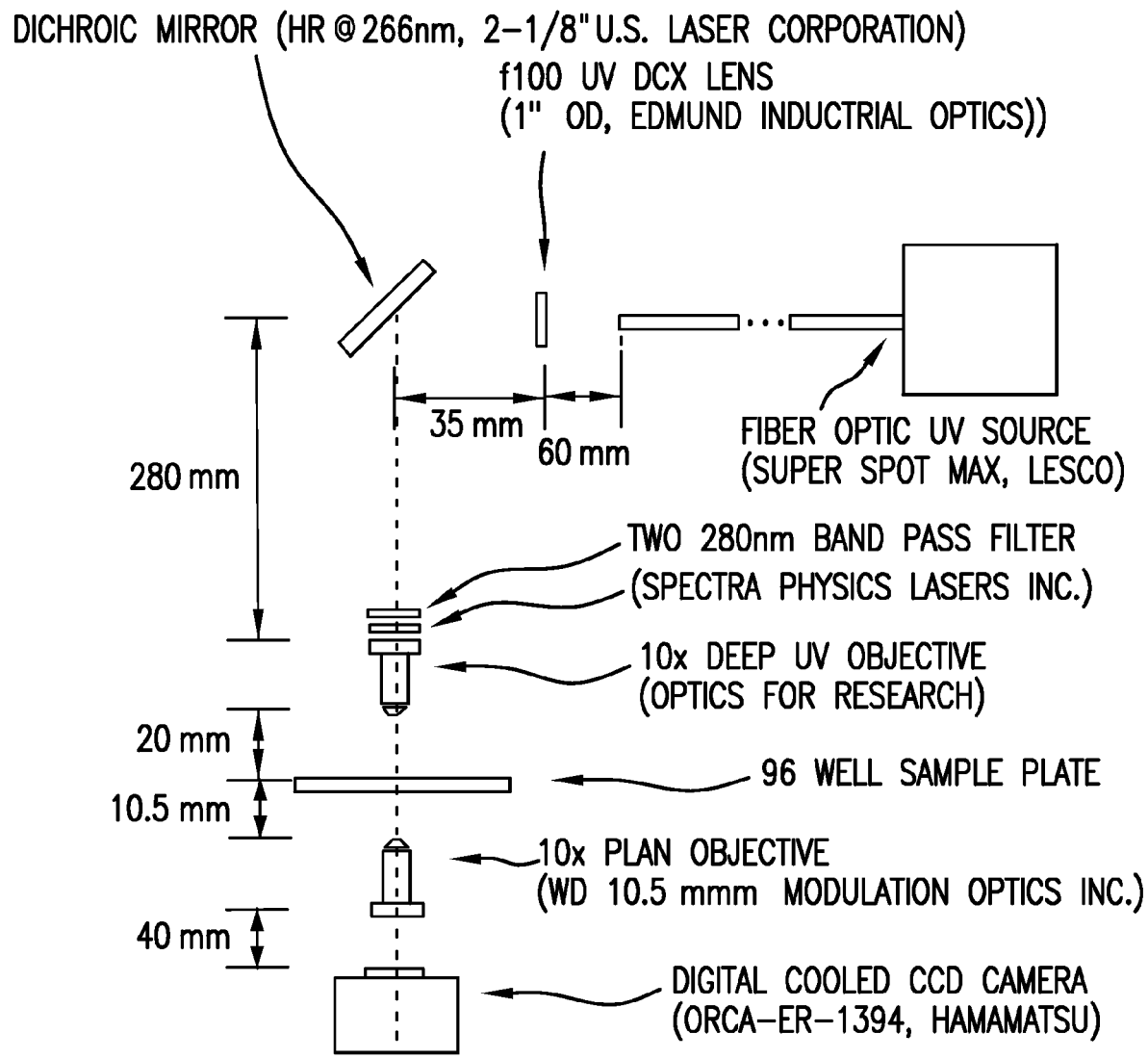
FIG. 3 illustrates a straight-through optical configuration, using another rendition of a UV fluorescence microscope in the methods of the present invention.
Figure 4:
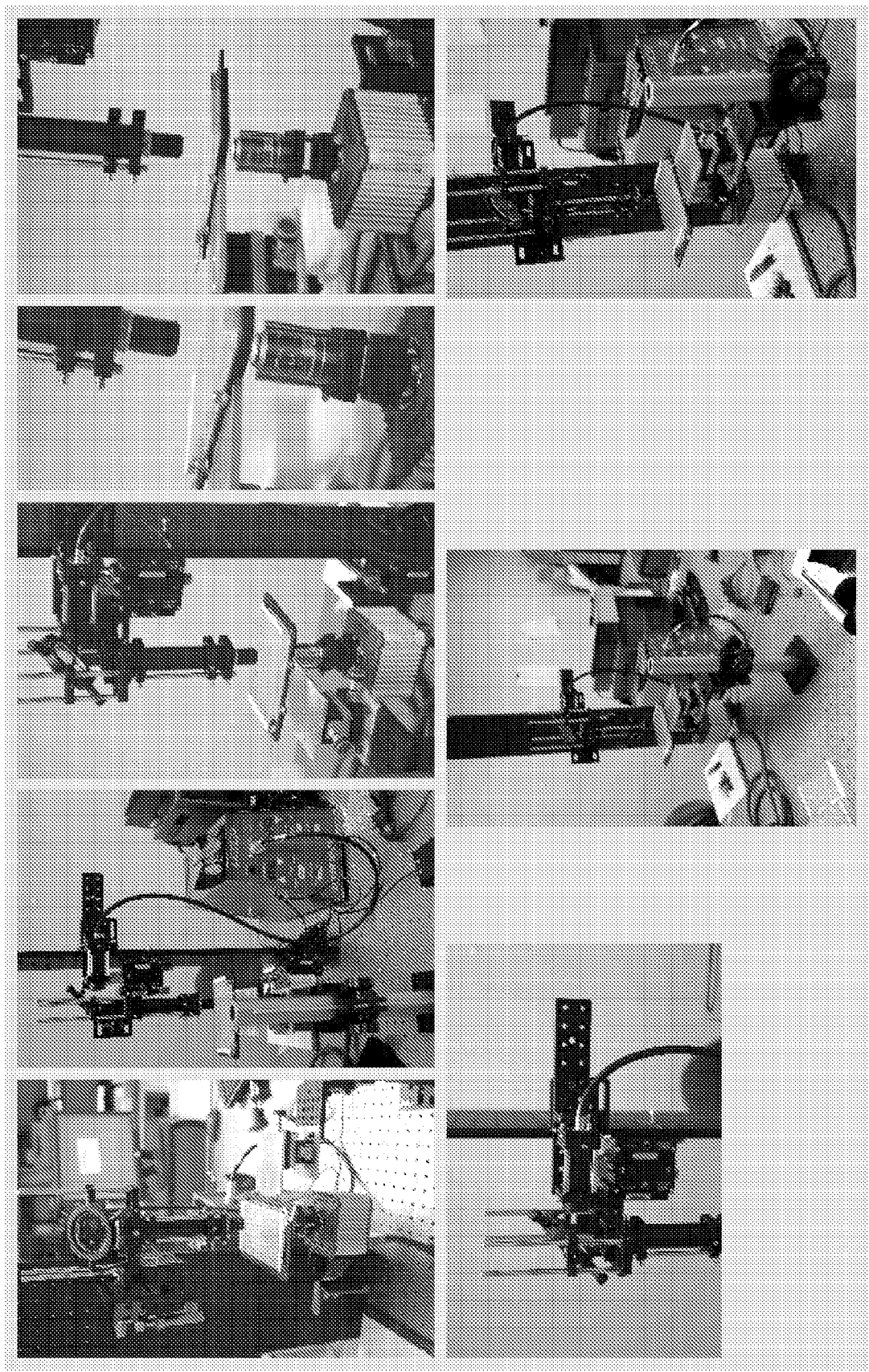
FIG. 4 includes photographs of the apparatus of FIG. 3, with its straight-through configuration.

FIG. 9 shows visible light images for these four samples, collected with an Olympus stereomicroscope Model SZX12 and an Olympus Model DP12 CCD camera, to be compared respectively with accompanying UV fluorescence images collected using the straight-through geometry setup of FIGS. 3 and 4. In this case, a vapor diffusion 96-well high-throughput crystallization plate covered in tape contained the sample. The well is about 2 mm across, and the protein solution droplet had a volume of 1 µl, and because it does not fill the well, its boundary was visible.

EXAMPLE IV

Distinguishing Non-Protein Crystals

Figure 10:
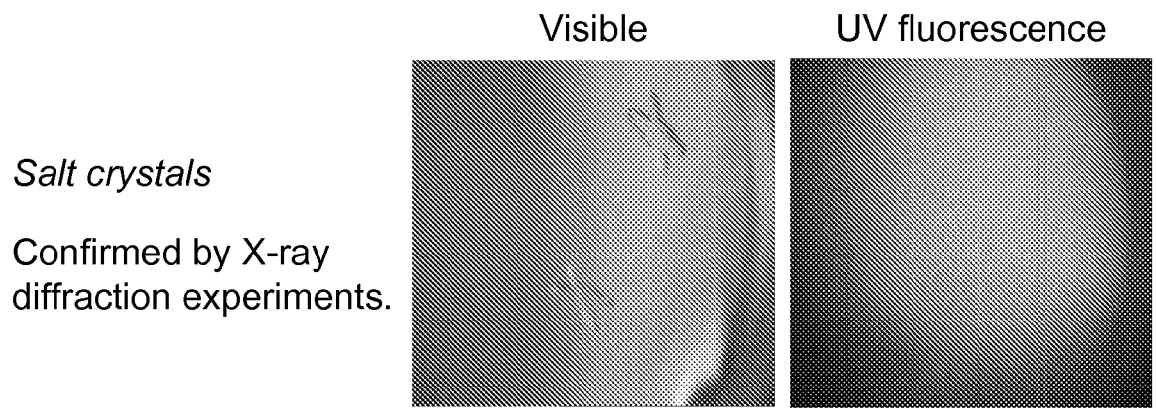
FIG. 10 shows crystals of salt, viewed with visible light, but disappearing under the conditions and with the same setup used for viewing intrinsic UV-excited fluorescence of protein crystals, using the epifluorescence configuration.

FIG. 10 illustrates salt crystals (confirmed by X-ray diffraction analysis) grown using 20 mg/ml lysozyme in 50 mM Tris, 100 mM ammonium sulfate, 10% glycerol, 1 mM DTT, 1 mM magnesium Acetate, 1 mM sodium azide pH 7.4 and mixed in a vapor diffusion crystallization in a 1:1 ratio with 40% Polyethylene glycol 300, 0.2 M calcium acetate, 0.1 M cacodylate pH 6.5 and equilibrated against a reservoir (100 µL) containing 40% Polyethylene glycol 300, 0.2 M calcium acetate, 0.1 M cacodylate pH 6.5. The crystals were grown at 17° C. over a few days. In particular, FIG. 10 shows a visible light image collected by illuminating from the side with visible light and using the visible CCD camera of the setup in FIG. 2. A salt crystal (confirmed later by X-ray diffraction) is clearly visible. The sample was subsequently imaged with epifluorescence on the same stand, and the sample's intrinsic fluorescence, if any, should have been excited through the objective lens. This same lens is used to collect any emission and pass the image to the CCD detector. In fact, in the second image of FIG. 10, the fluorescence-mode image, which is designed to be specific for protein, the salt crystals disappeared and were invisible. In this case, a vapor diffusion 96-well high-throughput crystallization plate, covered in tape, contained the sample.

EXAMPLE V

Distinguishing Non-Protein Crystals in the Presence of Protein Crystals

Figure 11:
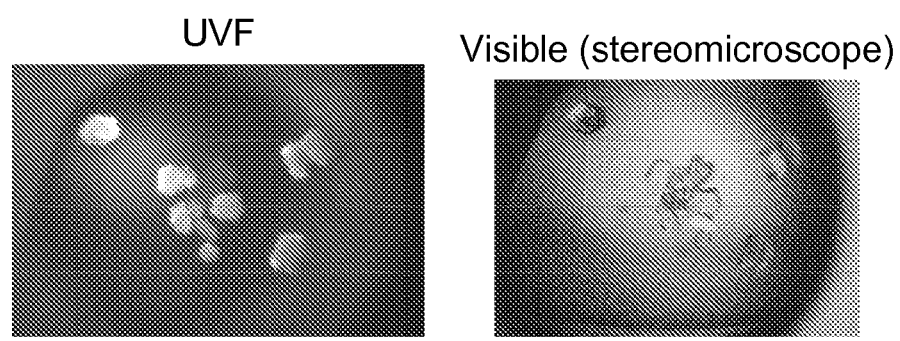
FIG. 11 shows crystals of salt, together with glucose isomerase, viewed with visible and intrinsic UV-excited fluorescence using the straight-through geometry.

As a demonstration of distinguishing protein and salt crystals, known salt crystals (X-shaped pair near center of image) grown as described in Example IV, were transferred by a nylon fiber loop over to a wellplate with glucose isomerase crystals grown from 30% MPD, 0.1 M Na cacodylate pH 6.5 and 0.2 M magnesium acetate. FIG. 11 shows a visible light image collected with an Olympus stereomicroscope Model SZX12 and an Olympus Model DP12 CCD camera, and UV fluorescence was imaged with the straight-through geometry setup of FIGS. 3 and 4. In this case, a vapor diffusion 96-well high-throughput crystallization plate, covered in tape, contained the sample. In the UV fluorescence image, all of the protein crystals can be seen easily as bright objects, while the salt crystals are only faintly visible because they do not fluoresce.

EXAMPLE VI

Distinguishing Crystals of a Target Protein in Metabolic Disease Research

Figure 12:
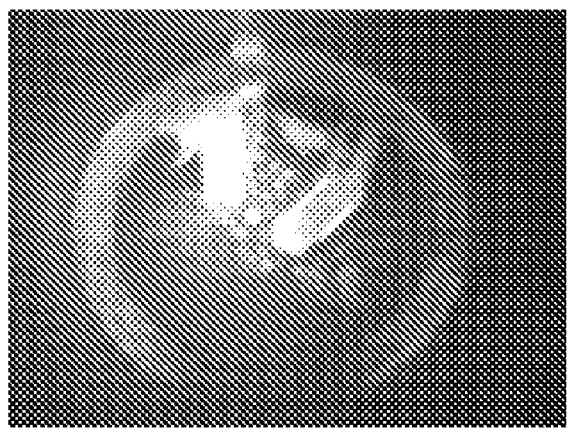
FIG. 12 shows human protein tyrosine phosphatase 1B crystals viewed with visible and intrinsic UV-excited fluorescence using the straight-through geometry.
Figure 12:
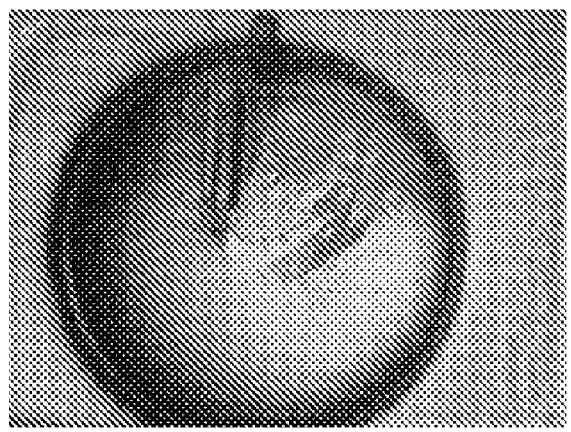

FIG. 12 illustrates human protein tyrosine phosphatase 1B crystals grown according to the method of Puius et al. (Puius, Y. A. et al., *Proc. Natl. Acad. Sci., USA* 94, 13420-13425 (1997); as modified by Szczepankiewicz, B. G. et al., *J. Am. Chem. Soc.* 125, 4087-4096 (2003)). In summary, crystals were grown at 4° C. by vapor diffusion using 3-4 mg/ml of protein with 2-4 mM DTT in 10 mM Tris-HCl, pH 7.5 and 25 mM NaCl mixed in a 1:1 ratio with 0.1 M HEPES pH 7.0-7.5, 0.2 M magnesium acetate, 12-14% polyethylene glycol 8000 and equilibrated over 1 ml of 0.1M HEPES pH 7.0-7.5, 0.2 M magnesium acetate, 12-14% polyethylene glycol 8000. In particular, FIG. 12 shows a visible light image collected with an Olympus stereomicroscope Model SZX12 and an Olympus Model DP12 CCD camera, and UV fluorescence was imaged with the straight-through geometry setup of FIGS. 3 and 4. In this case, the crystals were grown in a Linbro plate using the hanging drop method. For imaging the crystals were transferred to a 96 well vapor diffusion plate with tape covering the samples.

EXAMPLE VII

Distinguishing protein crystals in the presence of non-protein crystals

Figure 15A:
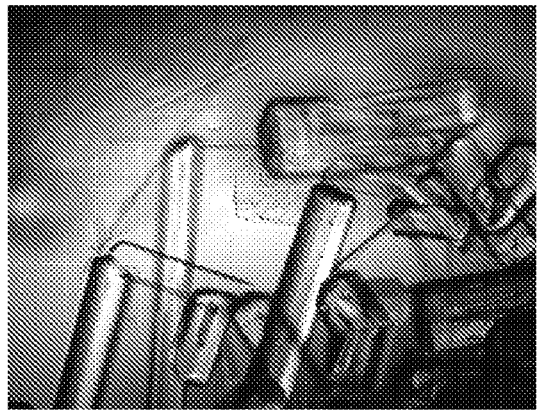
FIG. 15(a) illustrates visible imaging with a preparation containing xylanase and ammonium sulfate crystals.
Figure 15B:
FIG. 15(b) shows for comparison ultraviolet fluorescent imaging on the same preparation.
Figure 16A:
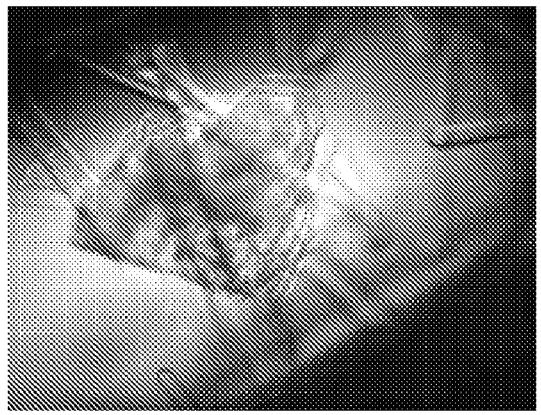
FIG. 16(a) illustrates visible imaging with a preparation containing xylanase and magnesium sulfate crystals.
Figure 16B:
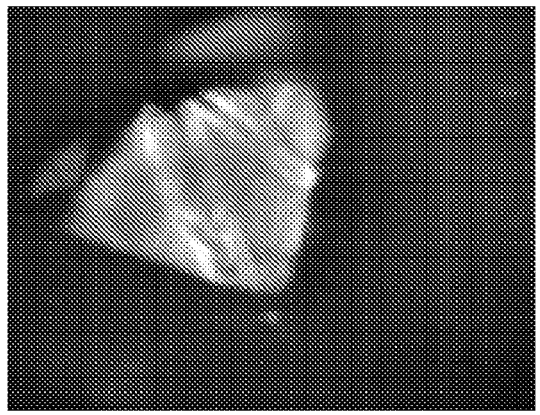
FIG. 16(b) shows for comparison ultraviolet fluorescent imaging on the same preparation.

Xylanase purchased from Hampton Research, Aliso Viejo, Calif.) was dissolved in distilled water to give a concentration of 10 mg/ml. Crystals were grown by vapor diffusion using a reservoir solution of 1.4 M sodium/potassium phosphate, pH 8.2, and a drop composition of 2 µL of protein solution and 2 µL of reservoir solution, at 17° C. The xylanase crystals were transferred to saturated solutions of ammonium sulfate and magnesium sulfate, which contained crystals of those respective salts. Regions of the drop, where xylanase and salt crystals were present, were selected for imaging, based on the known morphology and location of transfer of the xylanase crystals. The drops were contained in a 96 well plate (CrystalQuick plate, round bottom well, Greiner Bio-one Inc., Longwood, Fla.) covered with ClearSeal film (Hampton Research, Aliso Viejo, Calif.) and imaged using a straight-through geometry. FIG. 15(*a*) shows the visible light view of xylanase crystals amongst ammonium sulfate crystals with FIG. 15(*b*) showing the ultraviolet fluorescent image collected (using the microscope of FIGS. 21 and 22). In the ultraviolet fluorescent image of FIG. 15(*a*), the protein crystals are readily distinguishable and identifiable. FIG. 16(*a*) shows the visible light view of xylanase crystals amongst magnesium sulfate crystals with FIG. 16(*b*) showing the ultraviolet fluorescent image collected using the microscope of FIGS. 21 and 22. Again, in the UV fluorescent image, the protein crystals are easily distinguishable and identifiable.

Figure 17A:
FIG. 17(a) represents visible imaging with a preparation containing trypsin and ammonium sulfate crystals.
Figure 17B:
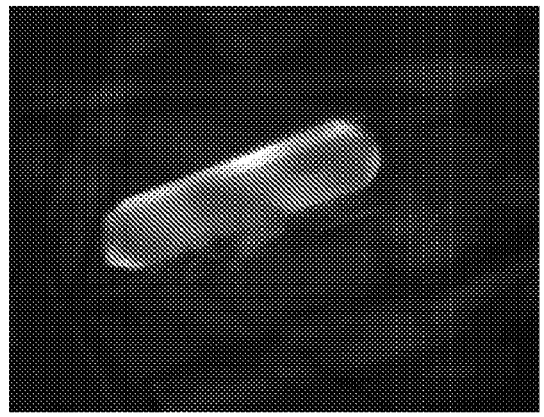
FIG. 17(b) shows for comparison ultraviolet fluorescent imaging on the same preparation.
Figure 18A:
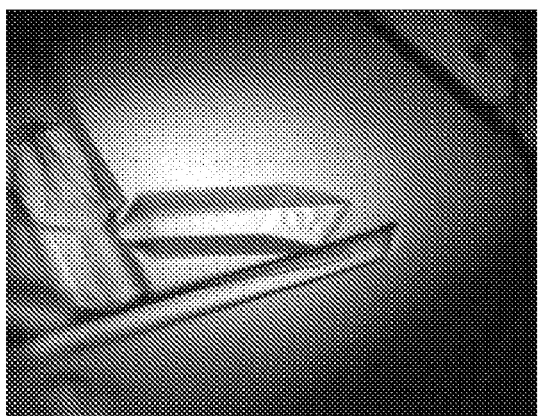
FIG. 18(a) represents an example of visible imaging with a preparation containing trypsin and ammonium sulfate crystals.
Figure 18B:
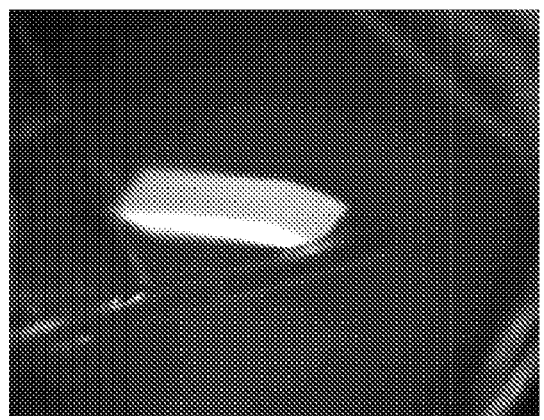
FIG. 18(b) shows for comparison ultraviolet fluorescent imaging on the same preparation.

Bovine trypsin (Sigma Chemicals, St. Louis, Mo.) was dissolved in 10 mM calcium chloride, 10 mg/ml benzamidine hydrochloride, 25 mM HEPES (pH 7.0) to give a protein concentration of 60 mg/ml. Crystals were grown by vapor diffusion using a reservoir of 0.1M Tris HCl pH 8.5, 2.0 M ammonium sulfate, and a drop composition of 2 µL of protein solution and 2 µL of reservoir solution, at 17° C. The trypsin crystals were transferred to saturated solutions of ammonium sulfate and magnesium sulfate, which contained crystals of those respective salts. Regions of the drop where trypsin and salt crystals were present were selected for imaging, based on the known morphology and location of transfer of the trypsin crystals. The drops were contained in a 96 well plate (CrystalQuick plate, round bottom well, Greiner Bio-one Inc., Longwood, Fla.) covered with ClearSeal film (Hampton Research, Aliso Viejo, Calif.) and imaged using a straight-through geometry. FIG. 17(*a*) shows the visible light view of trypsin crystals amongst ammonium sulfate crystals with FIG. 17(*b*) showing the ultraviolet fluorescent image collected using the microscope of FIGS. 21 and 22. In the UV fluorescent image, the protein crystals are easily distinguishable and identifiable. FIG. 18(*a*) shows the visible light view of trypsin crystals amongst magnesium sulfate crystals with FIG. 18(*b*) showing the ultraviolet fluorescent image collected using the microscope of FIGS. 21 and 22. Once again, using the UV fluorescent image alone, the protein crystals are easily distinguishable and identifiable.

EXAMPLE VIII

Distinguishing the presence of compounds bound to protein crystals

Figure 19:
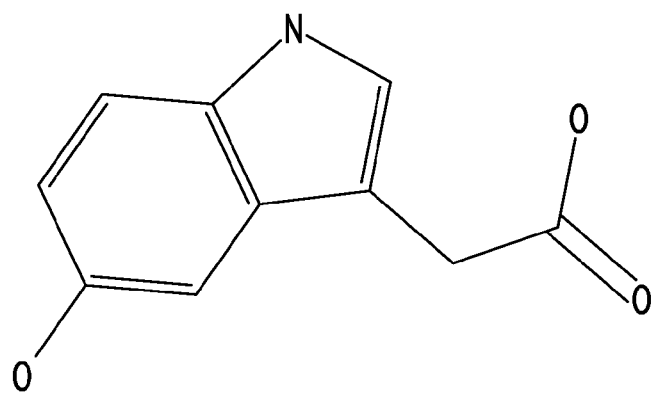
FIG. 19 illustrates the structure of 5-hydroxyindole-3-acetic acid used in Example VIII.
Figure 20A:
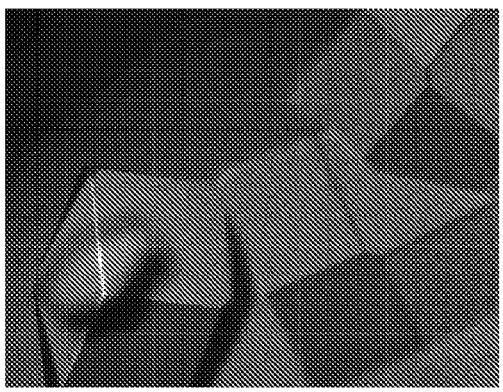
FIG. 20(a) represents visible imaging of lysozyme crystals.
Figure 20B:
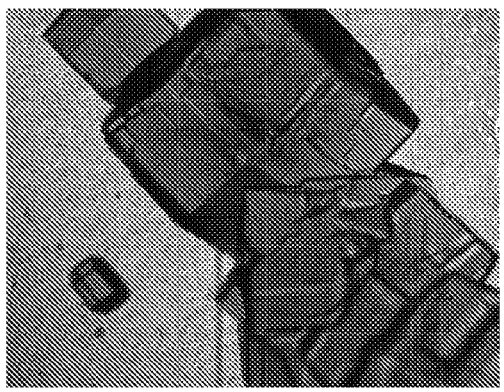
FIG. 20(b) represents lysozyme-compound complexed crystals viewed in visible light.
Figure 20C:
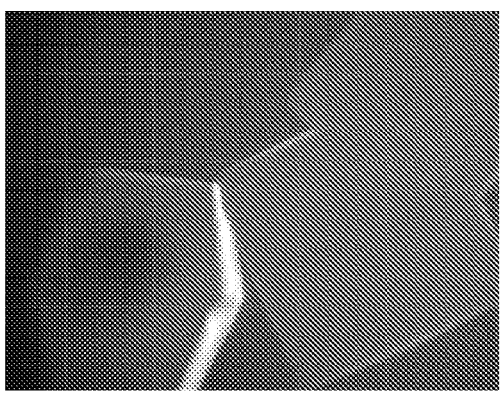
FIG. 20(c) represents ultraviolet fluorescence imaging of lysozyme crystals.
Figure 20D:
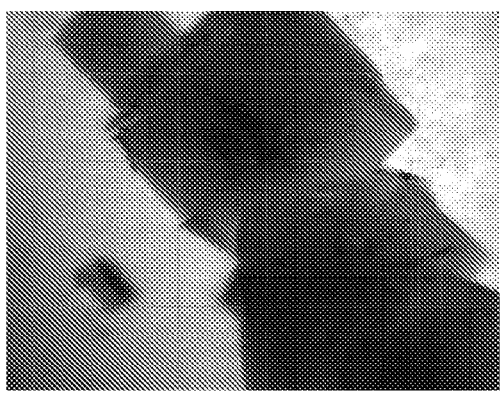
FIG. 20(d) represents lysozyme-compound complexed crystals viewed using ultraviolet fluorescence.

Lysozyme was prepared at a concentration of 50 mg/ml in 0.1 M sodium acetate buffer pH 4.65. Compound (5-hydroxyindole-3-acetic acid (Aldrich Handbook, p. 1360, 2005-2006; see also FIG. 19) was dissolved in DMSO (dimethylsulfoxide) to give a 1 M stock solution. This compound was chosen based on similar compounds reported to bind to lysozyme (Shinitsky et al., *Archives of Biochemistry and Biophysics* 116:332-343 (1966)). The compound was added to the lysozyme solution to give a 6:1 compound to protein ratio and a final DMSO content of 2% (v/v). The protein/compound solution was left to incubate at 4° C. for 48 h. Batch crystallization was performed by mixing 1 μL of the protein solution and 1 μL of 10% (w/v) sodium chloride, 0.1 M sodium acetate pH 4.65, to give a crystallization solution of 25 mg/ml protein, 0.1 M sodium acetate pH 4.65 and 5% (w/v) sodium chloride. The crystallization drops were set up in a 96 well vapor diffusion plate (CrystalQuick plate, round bottom well, Greiner Bio-one Inc., Longwood, Fla.) covered with ClearSeal film (Hampton Research, Aliso Viejo, Calif.). To maintain the drop volume over time the reservoir was filled with 0.1 M sodium acetate pH 4.65 and 5% (w/v) sodium chloride. Both crystals of lysozyme and lysozyme complexed with 5-hydroxyindole-3-acetic acid were grown under these conditions at 22° C. The crystals were imaged using a straight-through geometry with the microscope of FIGS. 21 and 22. FIGS. 20(a) and 20(b) show the visible light images of the lysozyme and lysozyme complex crystals. FIGS. 20(c) and 20(d) show the ultraviolet fluorescent images of the lysozyme and lysozyme complex crystals. The lysozyme crystals fluoresce brightly. The presence of compound quenches the fluorescence showing the crystals to be dark. In this instance the presence of compound can be determined due to the difference in fluorescence between the samples.

What is claimed is:

1. A method of distinguishing a crystal from other matter within a biological sample comprising the steps of:
    a) exposing said biological sample to ultraviolet radiation (UV);
    b) detecting radiation emission from said exposed biological sample, wherein said emission is luminescence comprising fluorescence, polarized fluorescence or phosphorescence; and
    c) analyzing said emission of step b) by determining whether 1) said emission of said biological sample has changed in comparison to a sample comprising no crystal or 2) whether variations in said emission of said biological sample are greater than said sample comprising no crystal, said change or variations allowing said crystal to be distinguished from other matter within said biological sample.

2. The method of claim 1 wherein said ultraviolet radiation has a wavelength of less than 351 nm.

3. The method of claim 2 wherein said ultraviolet radiation has a wavelength of between 140 nm and 320 nm.

4. The method of claim 3 wherein said ultraviolet radiation has a wavelength of between 260 nm and 300 nm.

5. The method of claim 1 wherein said biological sample is selected from the group consisting of a protein, a peptide, a cofactor, a nucleic acid and a mixture thereof.

6. The method of claim 1 wherein said emission is luminescence intrinsic to said crystal.

7. A method of distinguishing a crystal from other matter within a biological sample comprising the steps of: a) exposing said biological sample to ultraviolet radiation; b) detecting scattered photons from said exposed biological sample, wherein the scattered photons are Raman shifted from an incident wavelength between 140 and 350 nm, Raman shifted from an incident wavelength between 200 and 270 nm or are of Brillouin type; and c) analyzing said scattered photons of step b) by determining whether 1) said scattered photons of said biological sample have changed in comparison to a sample comprising no crystal or 2) whether variations in said scattered photons of said biological sample are greater than said sample comprising no crystal, said change or variations allowing said crystal to be distinguished from other matter within said biological sample.

8. The method of claim 7 wherein said biological sample is selected from the group consisting of a protein, a peptide, a cofactor, a nucleic acid and a mixture thereof.

9. A method of determining whether a ligand within a crystal has bound to a receptor comprising the steps of:
    a) measuring UV-excited emission or UV scattered light from a crystal comprising a receptor to said ligand, prior to addition of said ligand;
    b) adding said ligand to said crystal;
    c) measuring emission of said crystal subsequent to addition of said ligand, wherein said emission is luminescence comprising fluorescence, polarized fluorescence or phosphorescence and the scattered light is Raman shifted or of the Brillouin type; and
    d) determining whether said ligand has bound to said receptor by comparing said emission of step a) with said emission of step c), a difference in emission indicating binding of said ligand to said receptor.

10. The method of claim 9 wherein said emission is luminescence intrinsic to said crystal.

11. A method of determining presence of a compound within a crystal comprising the steps of:
    a) determining reference UV-excited emission or UV scattered light spectrum of said compound for: 1) free compound or 2) free compound and compound bound to a receptor;
    b) measuring UV-excited emission or scattered UV light spectrum of a test crystal suspected of containing said compound bound to said receptor, wherein said emission is luminescence comprising fluorescence, polarized fluorescence or phosphorescence and the scattered UV light is Raman shifted or of the Brillouin type; and
    c) comparing said emission or spectrum of step b) with said reference emission, spectrum or spectra of step a), comparable spectrum of said compound bound to said receptor or deviation from free compound indicating presence of said compound within said test crystal, and comparable spectrum with said free compound or deviation from compound bound to protein indicating absence of said compound within said test crystal.

12. The method of claim 11 wherein said emission is luminescence intrinsic to said crystal.

13. A method of determining whether a ligand has bound to a receptor within a test crystal comprising the steps of:
    a) measuring UV-excited emission or UV scattered light of a first crystal and a second crystal, wherein said emission is luminescence comprising fluorescence, polarized fluorescence or phosphorescence and the and scattered light is Raman shifted or of the Brillouin type, and further wherein said first crystal comprises said receptor to said ligand, and said second crystal comprises the test crystal, said test crystal being suspected of comprising said ligand bound to said receptor; and b) determining whether said ligand has bound to said receptor in said second crystal by comparing said emission of said first crystal and said second crystal of step a), a difference in emission indicating binding of said ligand to said receptor of said test crystal.

14. The method of claim 13 wherein said emission is luminescence intrinsic to said first crystal and said second crystal.

* * * * *

UNITED STATES PATENT AND TRADEMARK OFFICE
CERTIFICATE OF CORRECTION

PATENT NO.         : 7,545,495 B2
APPLICATION NO.    : 11/321993
DATED              : June 9, 2009
INVENTOR(S)        : Kerry M. Swift, Edmund D. Matayoshi and Russell A. Judge It is certified that error appears in the above-identified patent and that said Letters Patent is hereby corrected as shown below:

Title Page,

Inventors, "Kerry M. Swift, Libertyville, IL (US), Edmund D. Matayoshi, Richmond, IL (US)," should read -- Kerry M. Swift, Libertyville, IL (US), Edmund D. Matayoshi, Richmond, IL (US), Russell A. Judge, Gurnee, IL (US) --.

Signed and Sealed this

Tenth Day of November, 2009

David J. Kappos
*Director of the United States Patent and Trademark Office*